US009364004B2

(12) United States Patent
Khodakovskaya et al.

(10) Patent No.: US 9,364,004 B2
(45) Date of Patent: Jun. 14, 2016

(54) METHOD OF USING CARBON NANOTUBES TO AFFECT SEED GERMINATION AND PLANT GROWTH

(75) Inventors: Mariya V. Khodakovskaya, Little Rock, AR (US); Alexandru S. Biris, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 849 days.

(21) Appl. No.: 13/509,487

(22) PCT Filed: Nov. 15, 2010

(86) PCT No.: PCT/US2010/002976
§ 371 (c)(1),
(2), (4) Date: May 11, 2012

(87) PCT Pub. No.: WO2011/059507
PCT Pub. Date: May 19, 2011

(65) Prior Publication Data
US 2012/0233725 A1 Sep. 13, 2012

Related U.S. Application Data

(60) Provisional application No. 61/281,131, filed on Nov. 13, 2009, provisional application No. 61/341,956, filed on Apr. 7, 2010.

(51) Int. Cl.
| | | |
|---|---|---|
| *A01H 3/00* | (2006.01) |
| *A01N 59/00* | (2006.01) |
| *A01C 1/02* | (2006.01) |
| *C05F 11/00* | (2006.01) |
| *A01N 37/18* | (2006.01) |
| *A01N 57/16* | (2006.01) |
| *C05D 9/00* | (2006.01) |
| *B82B 1/00* | (2006.01) |
| *B82Y 5/00* | (2011.01) |

(52) U.S. Cl.
CPC . *A01N 59/00* (2013.01); *A01C 1/02* (2013.01); *A01H 3/00* (2013.01); *A01N 37/18* (2013.01); *A01N 57/16* (2013.01); *C05D 9/00* (2013.01); *C05F 11/00* (2013.01); *B82B 1/00* (2013.01); *B82Y 5/00* (2013.01); *Y10S 71/904* (2013.01)

(58) Field of Classification Search
None
See application file for complete search history.

(56) References Cited

U.S. PATENT DOCUMENTS

| 4,448,796 A | 5/1984 | Wieser |
| 5,849,320 A | 12/1998 | Turnblad |
| 5,930,949 A | 8/1999 | Tsujimoto |
| 2002/0115565 A1 | 8/2002 | Asrar |
| 2005/0210744 A1 | 9/2005 | Watanabe |

OTHER PUBLICATIONS

Khodakovskaya et al (Sep. 2009, ACS Nano 3 (10): 3221-3227).*
Khodakovskaya et al (2009, ACS Nano 3(10): 3221-3227).*
Ma et al (2010, Science of the Total Environment 408:3053-3061).*
Husen and Siddiqi (2014, Journal of Nanobiotechnology 12(1): 1-17).*
Harrison, Benjamine, et al., Carbon Nanotube Applications for Tissue Engineering, Biomaterials (2007), vol. 28, p. 344-353.
Bradford, K.J., Water Relations in Seed Germination, Seed Development and Germination, 1995 by Marcel Dekker: New York, p. 351-396.
Yoshida, A, et al., Full Width at Half Maximum Intensity of the G Band in the First Order Raman Spectrum of Carbon Material as a Parameter for Graphitization, Carbon (2006), vol. 44, p. 2330-2335.
Oberdorster, Gunter, et al., Nanotoxicology an Emerging Discipline Evolving from Studies of Ultrafine Particles, Environmental Health Perspectives (Jul. 2005) vol. 113, p. 823-839.
Borm, Paul, et al., The Potential Risks of Nanomaterials: A Review Carried Out for ECETOC, Particle and Fibre Toxicology (Aug. 4, 2006), vol. 3, p. 1-12.
Paynam, Jayanth, et al., Biodegradable Nanoparticles for Drug and Gene Delivery to Cells and Tissue, Advanced Drug Delivery Reviews (2003), vol. 55, p. 329-347.
Chen, Robert J., et al., Noncovalent functionalization of carbon nanotubes for highly specific electronic biosensors, PNAS (Apr. 29, 2003), vol. 100, No. 9, p. 4984-4989.
Zanello, Laura, et al., Bone Cell Proliferation on Carbon Nanotubes, Nano Letters (2006), vol. 6, No. 3, p. 562-567.
Kam, Nadine, et al., Carbon Nanotubes as Multifunctional Biological Transporters and Near-Infrared Agents for Selective Caner Cell Destruction, Proceedings of the National Academy of Sciences (Aug. 16, 2005), vol. 102, No. 33, p. 11600-11605.
Pitsillides, Costas, et al., Selective Cell Targeting with Light-Absorbing Microparticles and Nanoparticles, Biophysical Journal (Jun. 2003), vol. 84, pp. 4023-4032.
Zharov, Vladimir, et al., Synergistic Enhancement of Selective Nanophototermolysis with Gold Nanoclusters: Potential for Cancer Therapy, Lasers in Surgery and Medicine (2005), vol. 37, p. 219-226.
Xia, Tian, et al., Comparison of the Abilities of Ambient and Manufactured Nanoparticles to Induce Cellular Toxicity According to an Oxidative Stress Paradigm, Nano Letters (2006), vol. 6, p. 1794-1807.
Liu, Zhuang, et al., Circulation and Long-Term Fate of Functionalized, Biocompatible Single-Walled Carbon Nanotubes in Mice Probed by Raman Spectroscopy, Proceedings of the National Academy of Sciences (Feb. 5, 2008), vol. 105, No. 5, p. 1410-1415.
Geiser, Marianne, et al., Ultrafine Particles Cross Cellular Membranes by Nonphagocytic Mechanisms in Lungs and in Cultured Cells, Environmental Health Perspectives (Nov. 2005) vol. 113, No. 11, p. 1555-1560.

(Continued)

*Primary Examiner* — Stuart F Baum
(74) *Attorney, Agent, or Firm* — Richard Blakely Glasgow

(57) ABSTRACT

A method of increasing the probability and rate of seed germination, increasing vegetative biomass, and increasing water uptake in seeds, in which a seed is introduced to an effective concentration of carbon nanomaterial. The effective concentration of carbon nanomaterial is 10-200 µg/mL.

7 Claims, 16 Drawing Sheets

(56) References Cited

OTHER PUBLICATIONS

Torney, Francois, et al., Mesoporous Silica Nanoparticles Deliver DNA and Chemicals into Plants, Nature Manotechnology (May 2007) vol. 2, p. 295-300.

Liu, Qiaoling, et al., Carbon Nanotubes as Molecular Transporters for Walled Plant Cells, Nano Letters (2009), vol. 9, No. 3, p. 1007-1010.

Gonzalez-Melendi, P, et al., Nanoparticles as Smart Treatment-delivery Systems in Plants: Assessment of Different Techniques of Microscopy for their Visualization in Plant Tissues, Annals of Botany (Nov. 12, 2007), vol. 101, p. 187-195.

Matsumara, Sachiko, et al., Dispersion of Cisplatin-Loaded Carbon Nanohorns with a Conjugate Comprised of an Artificial Peptide Aptamer and Polyethylene Glyocl, Mol. Pharmaceutics (2007), p. 723-729 (abstract).

Serrato-Valenti, G., et al., Structure and Histochemisry of Embryo Envelope Tissues in the Mature Dry Seed and Early Germination of Phacelia tanacetifolia, Annals of Botany (2000), vol. 85, p. 625-634.

Wierzbicka, Malgorzata, et al., The Effect of Lead on Seed Imbibition and Germination in Different Plan Species, Plant Science (1998), vol. 137, p. 155-171.

Dresselhaus, M.S., et al., Raman Spectroscopy on Isolated Single Wall Carbon Nanotubes, Carbon (2002), vol. 40, p. 2043-2061.

Jorio, A, et al., Characterizing Carbon Nanotube Samples with Resonance Raman Scattering, New Journal of Physics (2003), vol. 5, p. 139.1-139.17.

Dresselhaus, M.S., et al., Raman Spectroscopy of Carbon Nanotubes, Physics Reports (2005), vol. 409, p. 47-99.

Torney, Francois, et al., Mesoporous silica nanoparticles deliver DNA and chemicals into plants, Nature Nanotechnology (May 2007), vol. 2, p. 295-300.

Klaine, Stepehen J., et al., Nanomaterials in the Environment: Behavior, Fate, Bioavailability, and Effects, Environmental Toxicology and Chemistry (2008), vol. 27, No. 9, p. 1825-1851.

Zheng, Lei, et al., Effect of Nano-$TiO_2$ on Strength of Naturally Aged Seeds and Growth of Spinach, Biological Trace Element Research (2005), vol. 104, p. 83-91.

Lin, Daohui, et al., Phytotoxicity of Nanoparticles: Inhibition of Seed Germination and Root Growth, Environmental Pollution (2007), vol. 150, p. 243-250.

Yang, Ling, et al., Particle Surface Characteristics May Play an Important Role in Phytotoxicity of Alumina Nanoparticles, Toxicology Letters (2005), vol. 158, p. 122-132.

Canas, Jaclyn E., et al., Effects of Functionalized and Nonfucntionalized Single-Walled Carbon Nanotubes on Root Enlongation of Select Crop Species, Environmental Toxicology and Chemistry (2008) vol. 27, No. 9, p. 1922-1931.

Waggoner, Paul E., et al., Water Update and Water Diffusivity of Seeds, Plant Physiology (1976), vol. 57, p. 153-156.

International Search Report and Written Opinion, International Application No. PCT/US2010/02976 (Jan. 20, 2011).

Tyerman, S.D., et al., Plant Aquaporins: Their Molecular Biology, Biophysics and Significance for Plant Water Relations, Journal of Experimental Botany (Jun. 1999), vol. 50, Special Issue, p. 1055-1071.

Liu, Hong-Yan, et al., The Role of Water Channel Proteins and Nitric Oxide Signaling in Rice Seed Germination, Cell Research (2007), vol. 17, p. 638-649.

\* cited by examiner (A)
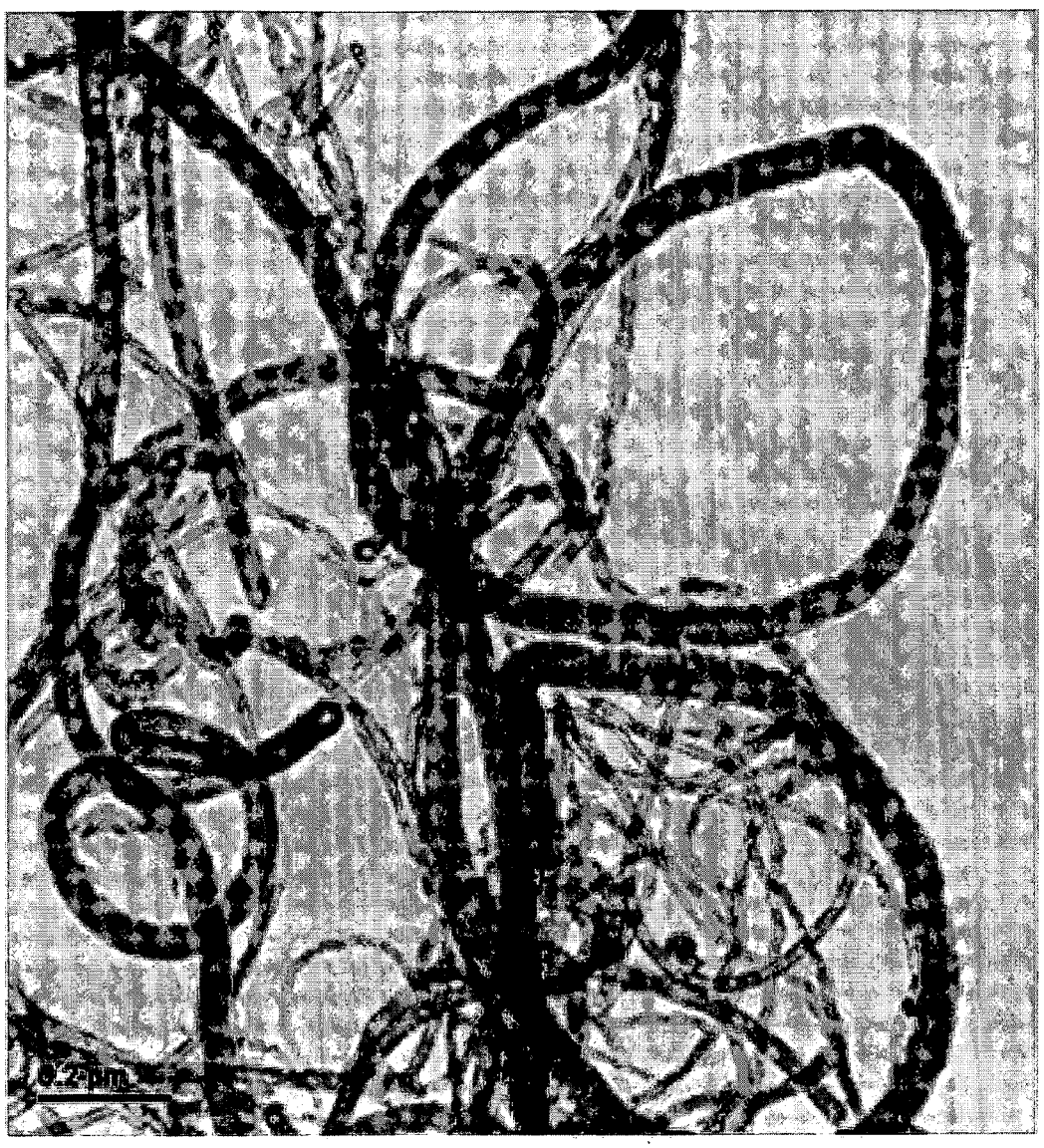
Figure 1-A (B)
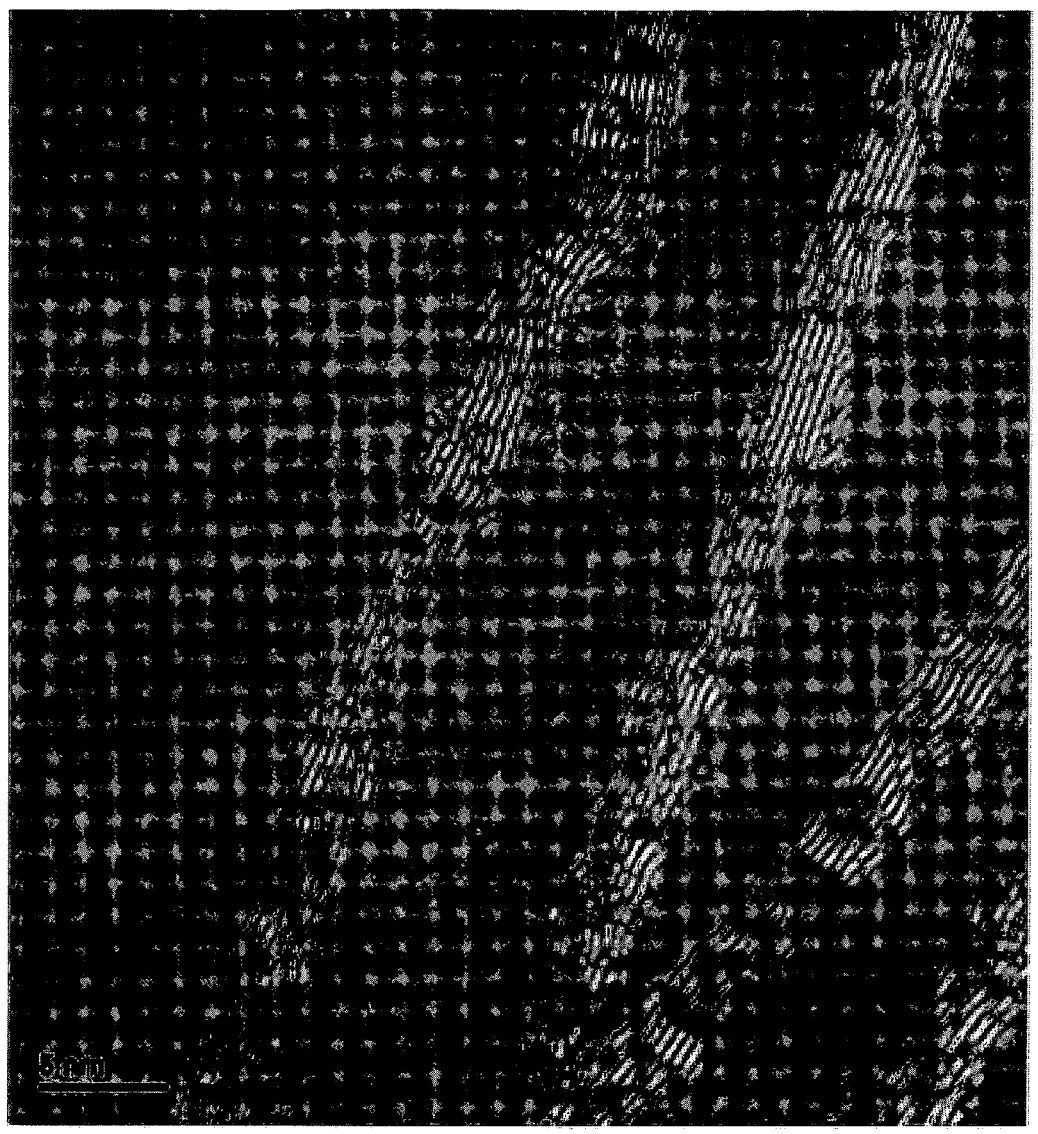
Figure 1-B

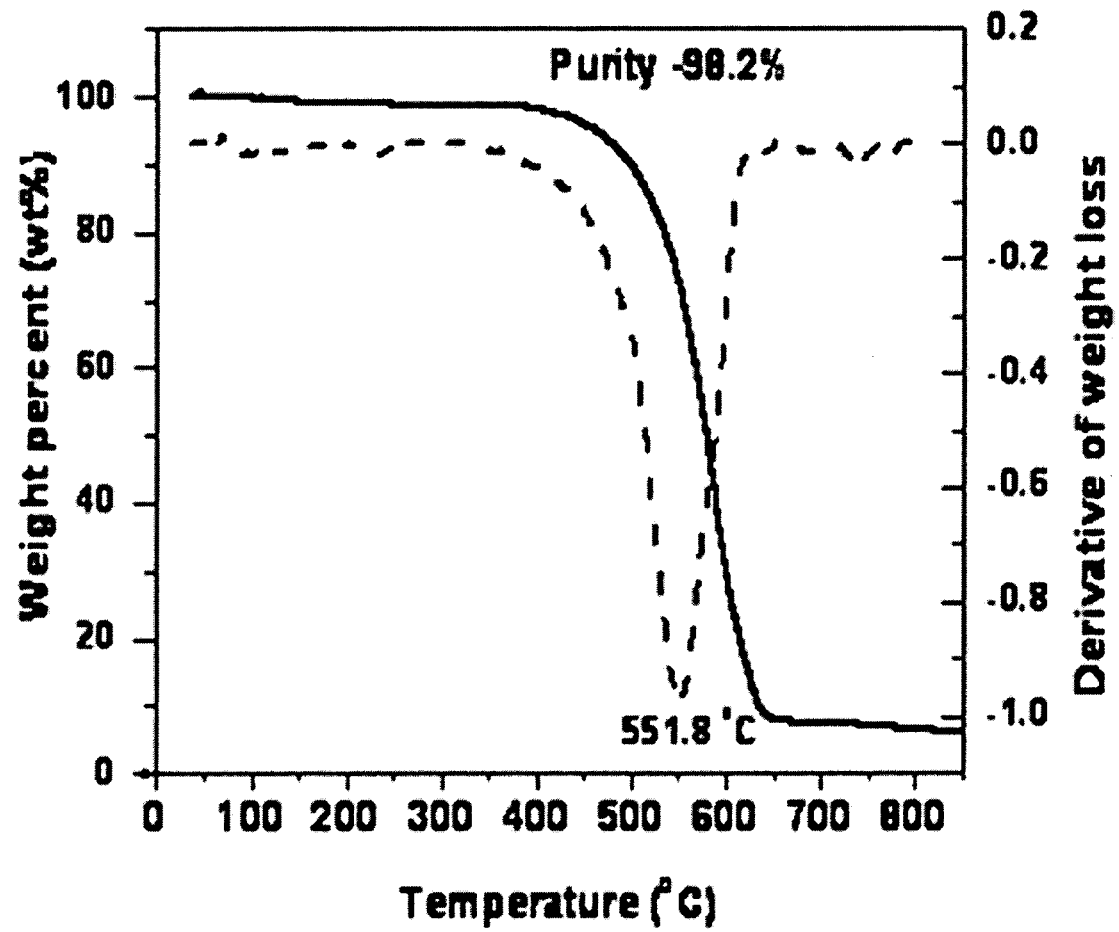
Figure 1-C

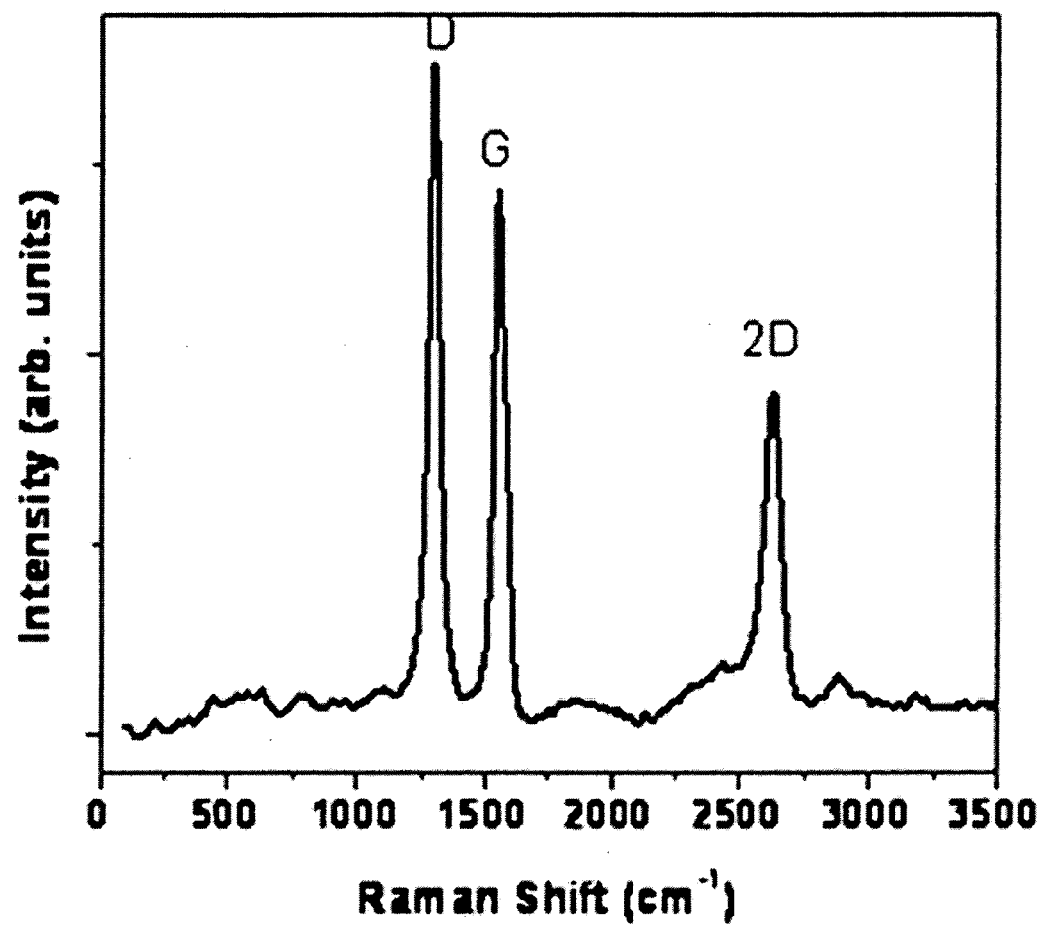
Figure 1-D

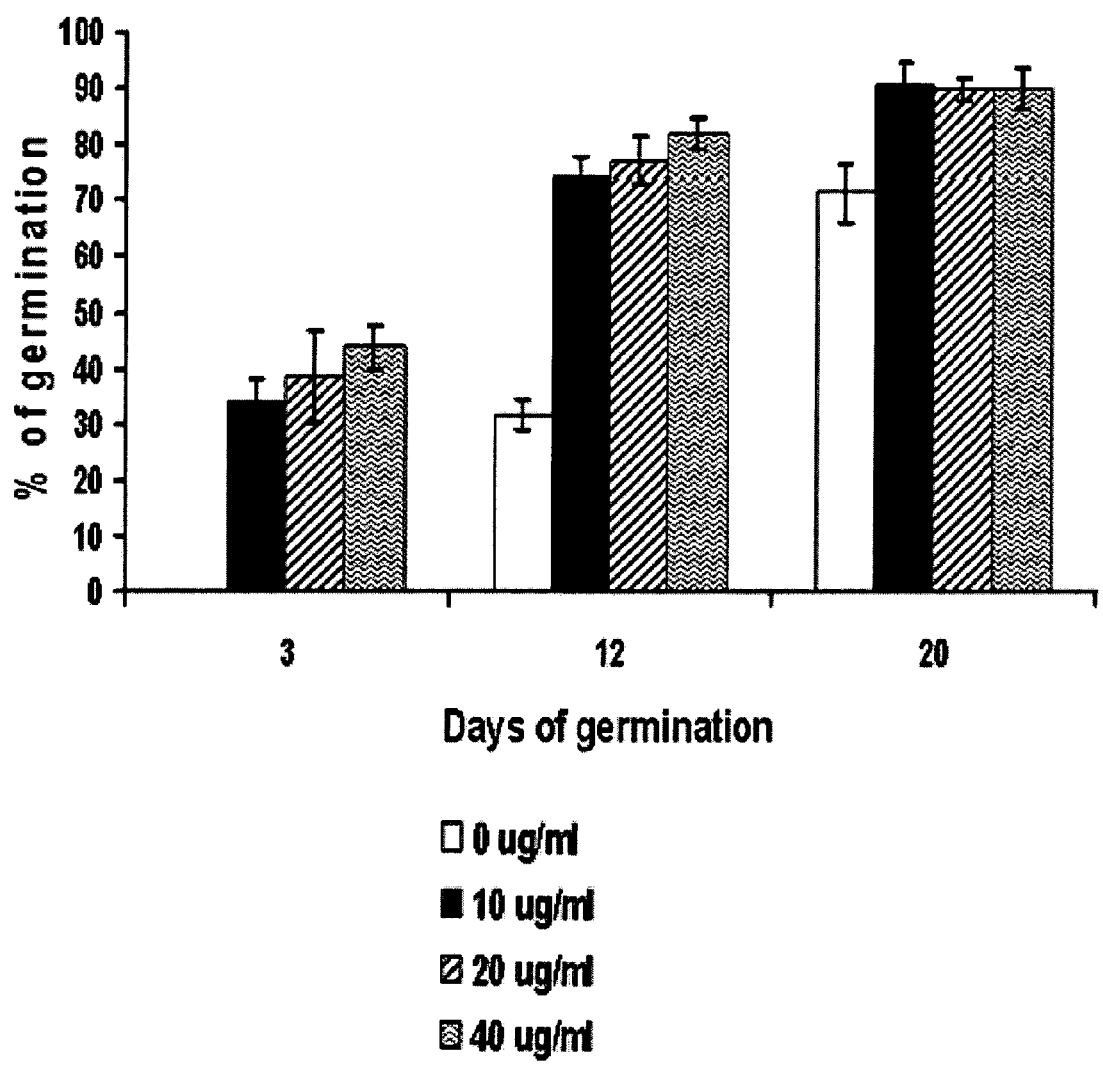
Figure 2-A

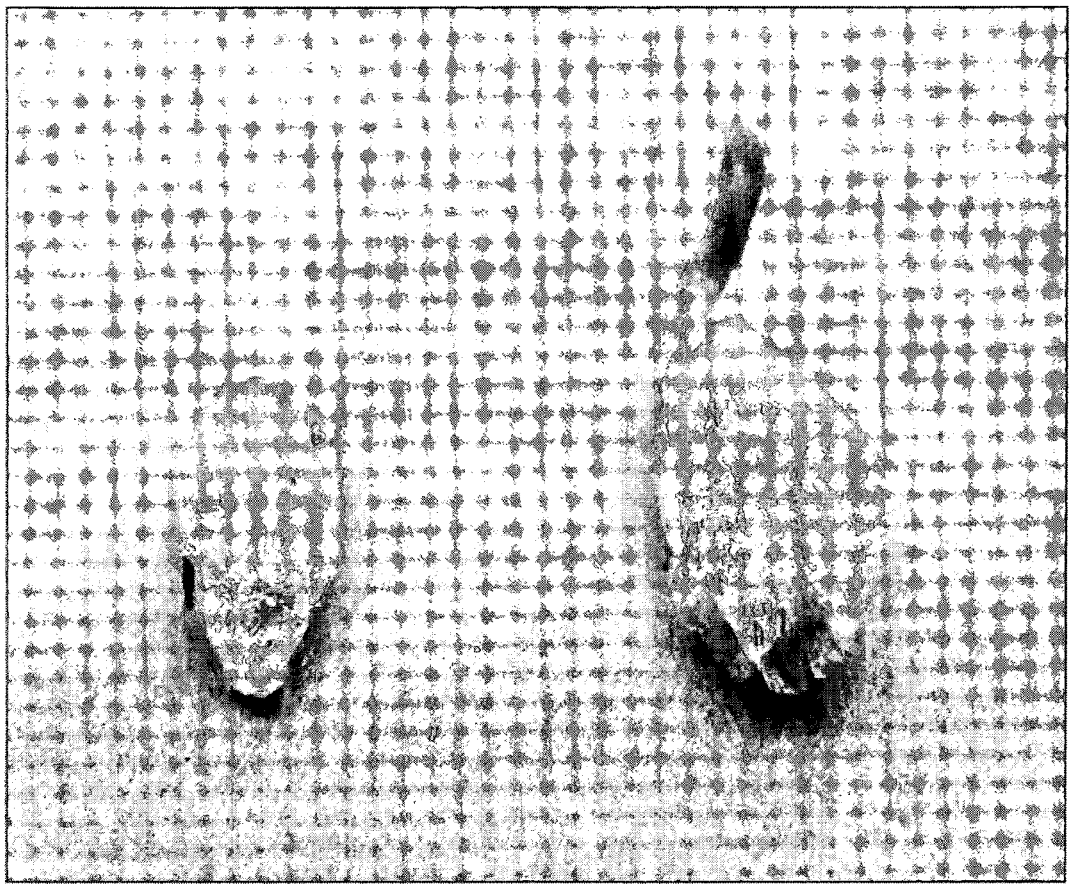
Figure 2-B

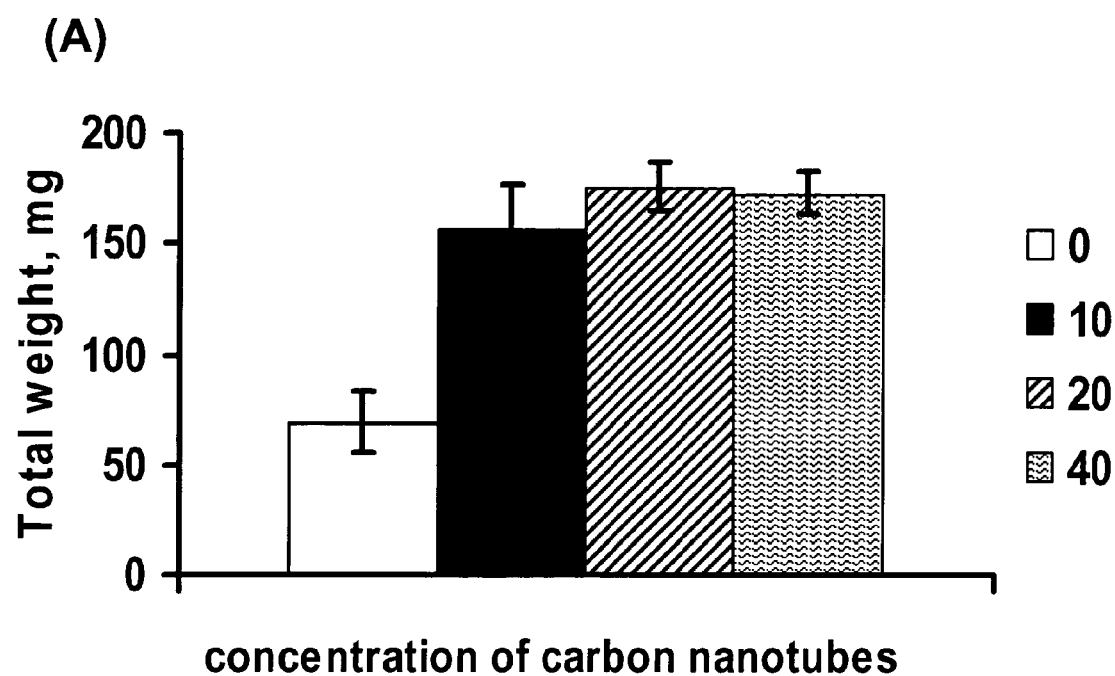
Figure 3-A

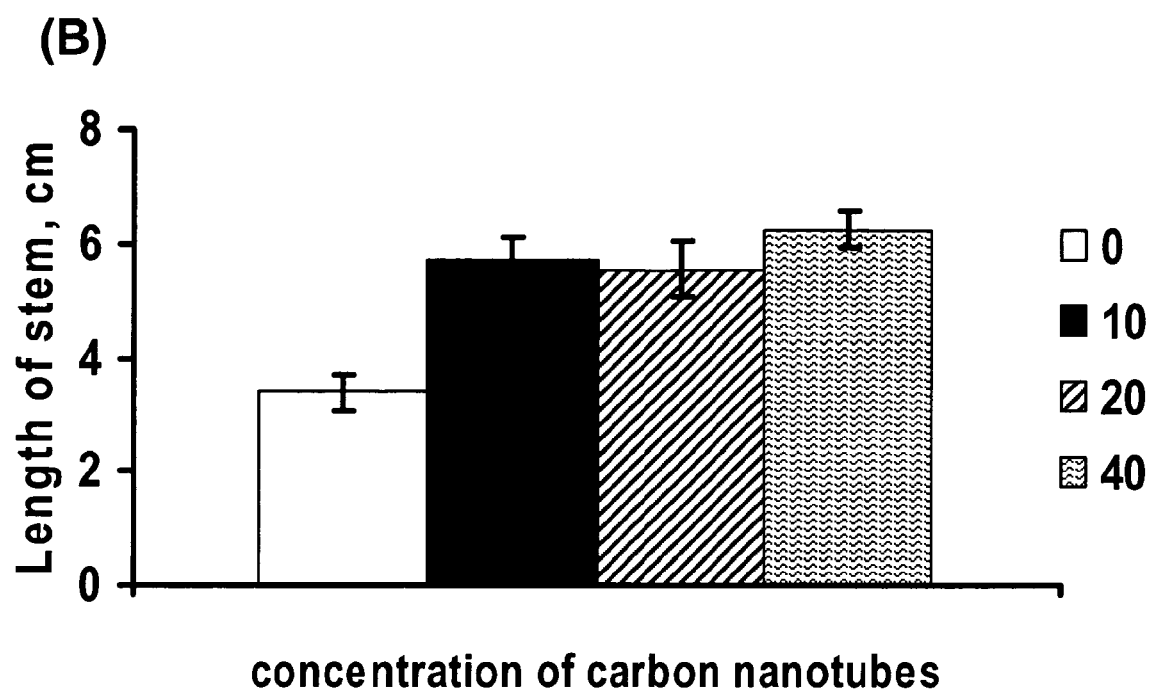
Figure 3-B

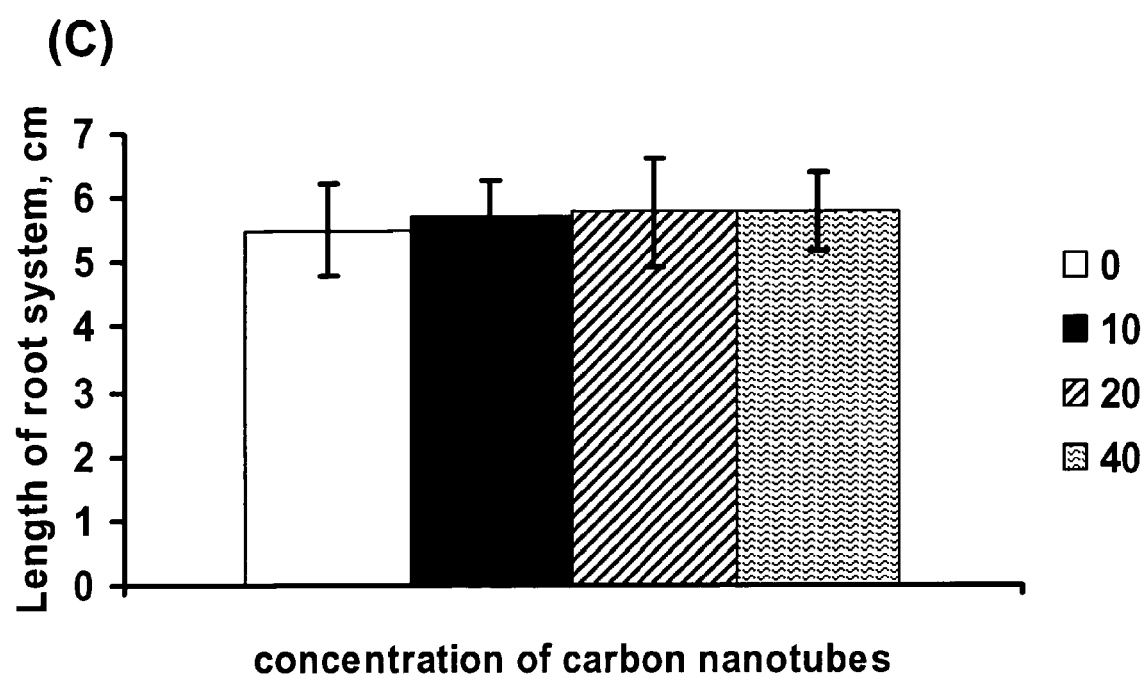
Figure 3-C

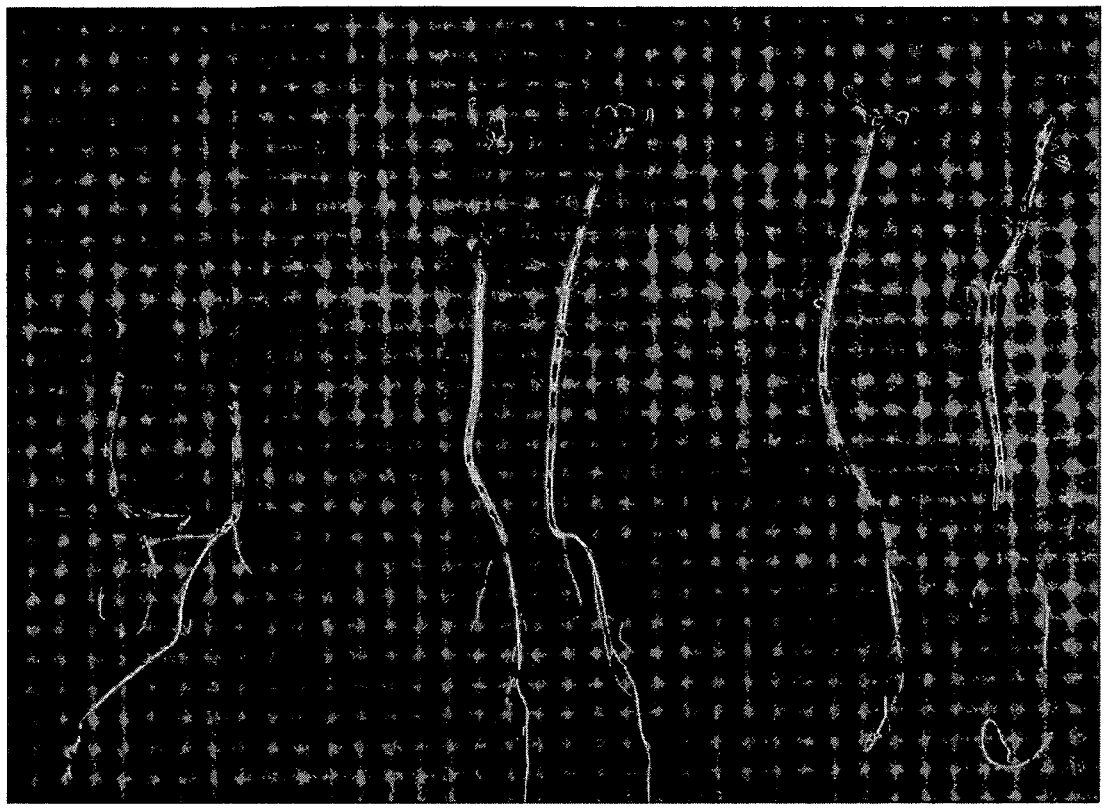
Figure 3-D (E)
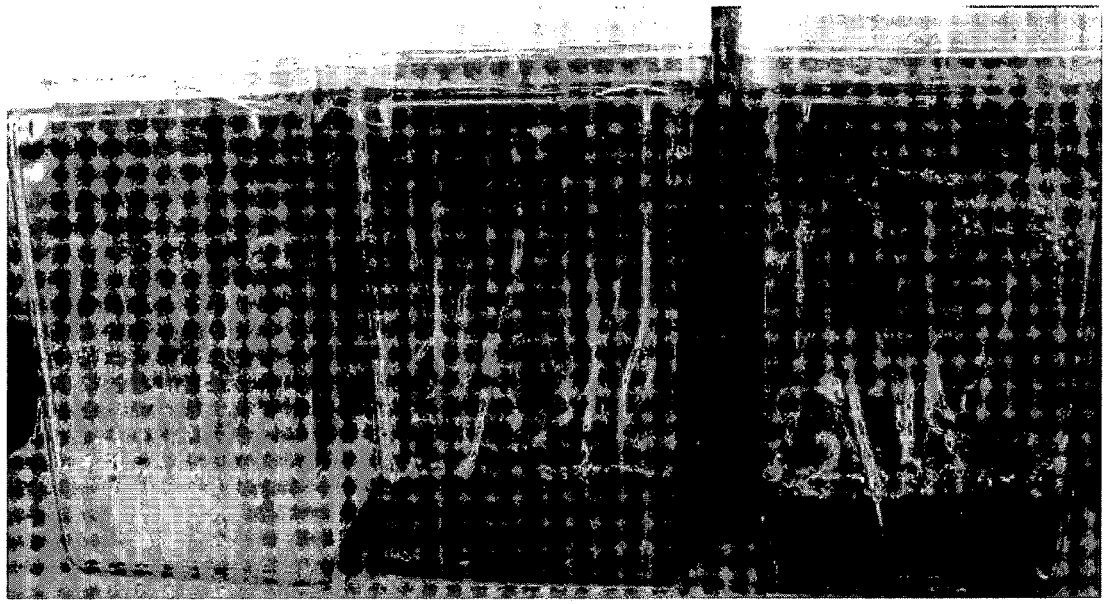
Concentration of nanotubes in growth medium
Figure 3-E

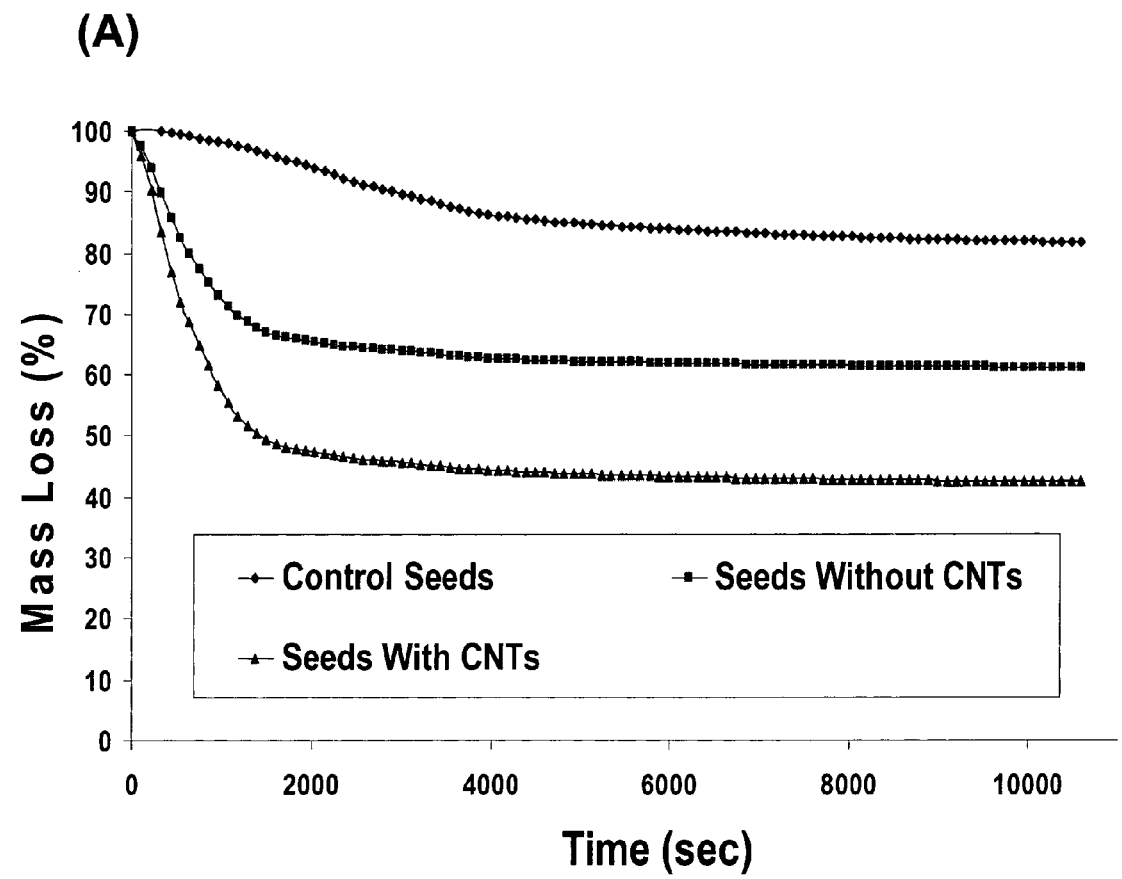
Figure 4-A

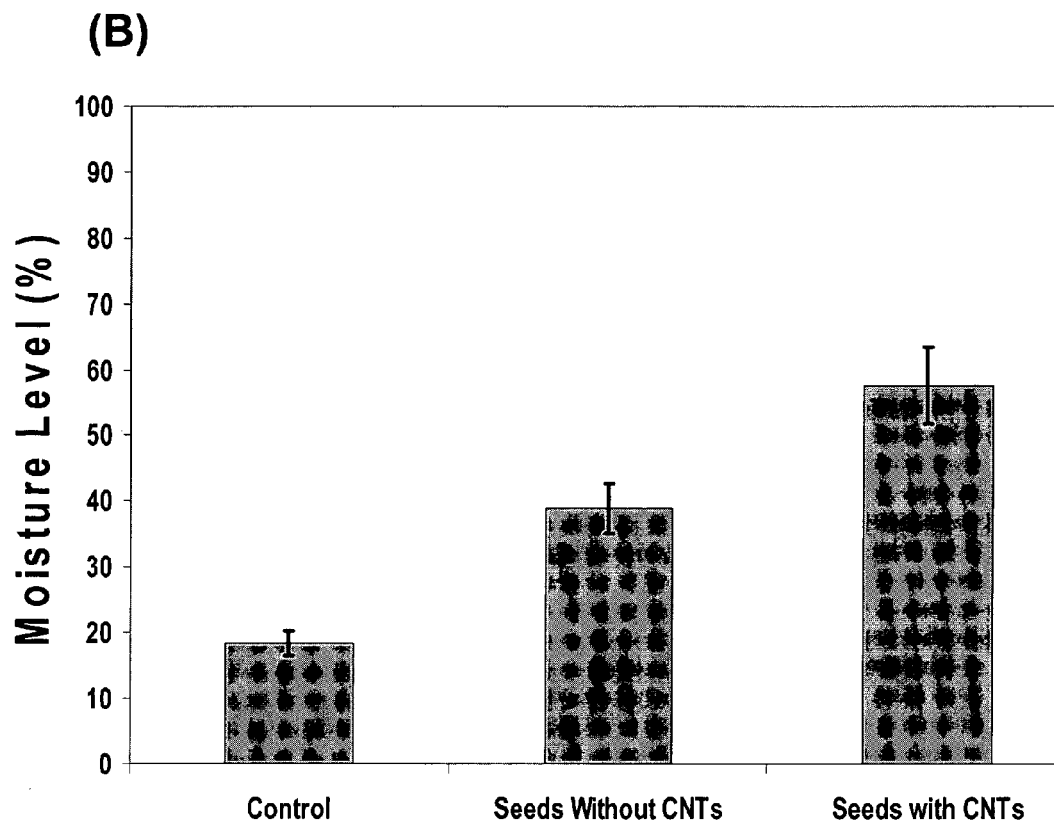
Figure 4-B

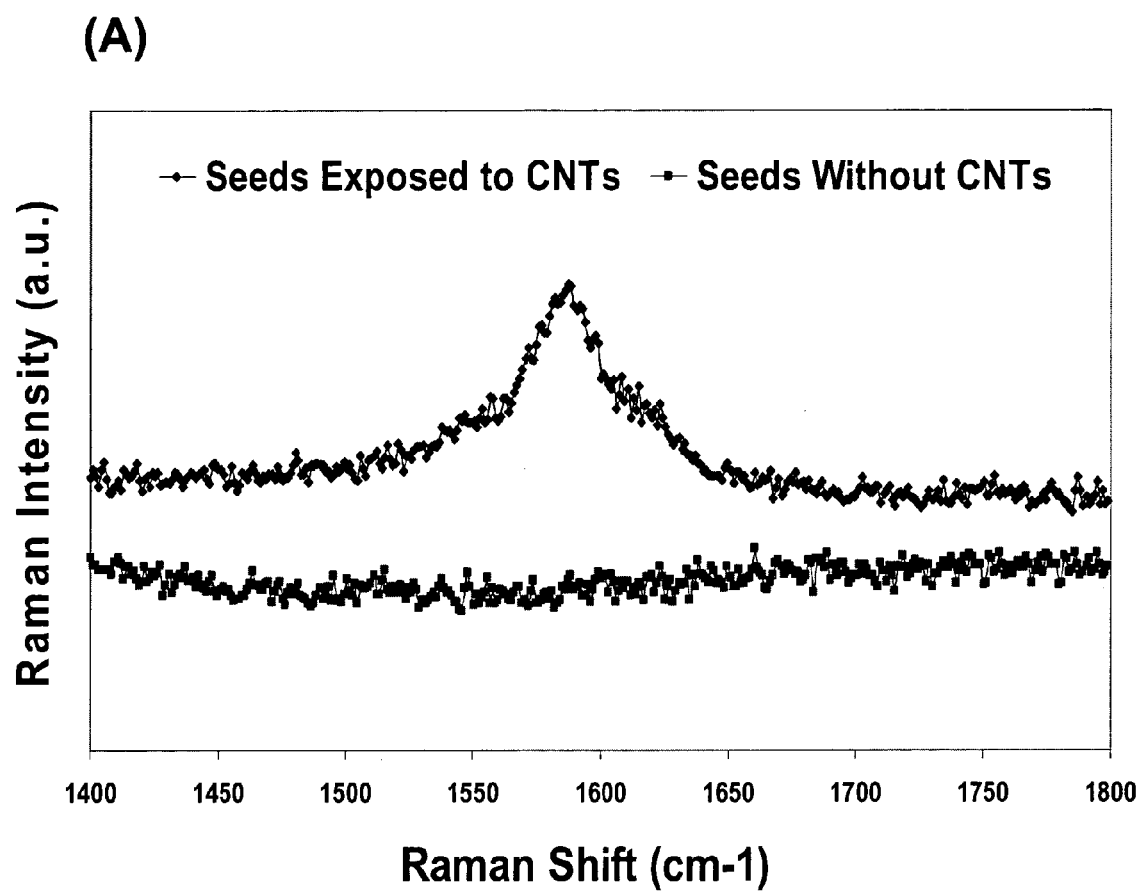
Figure 5-A (B)
Figure 5-B (C)
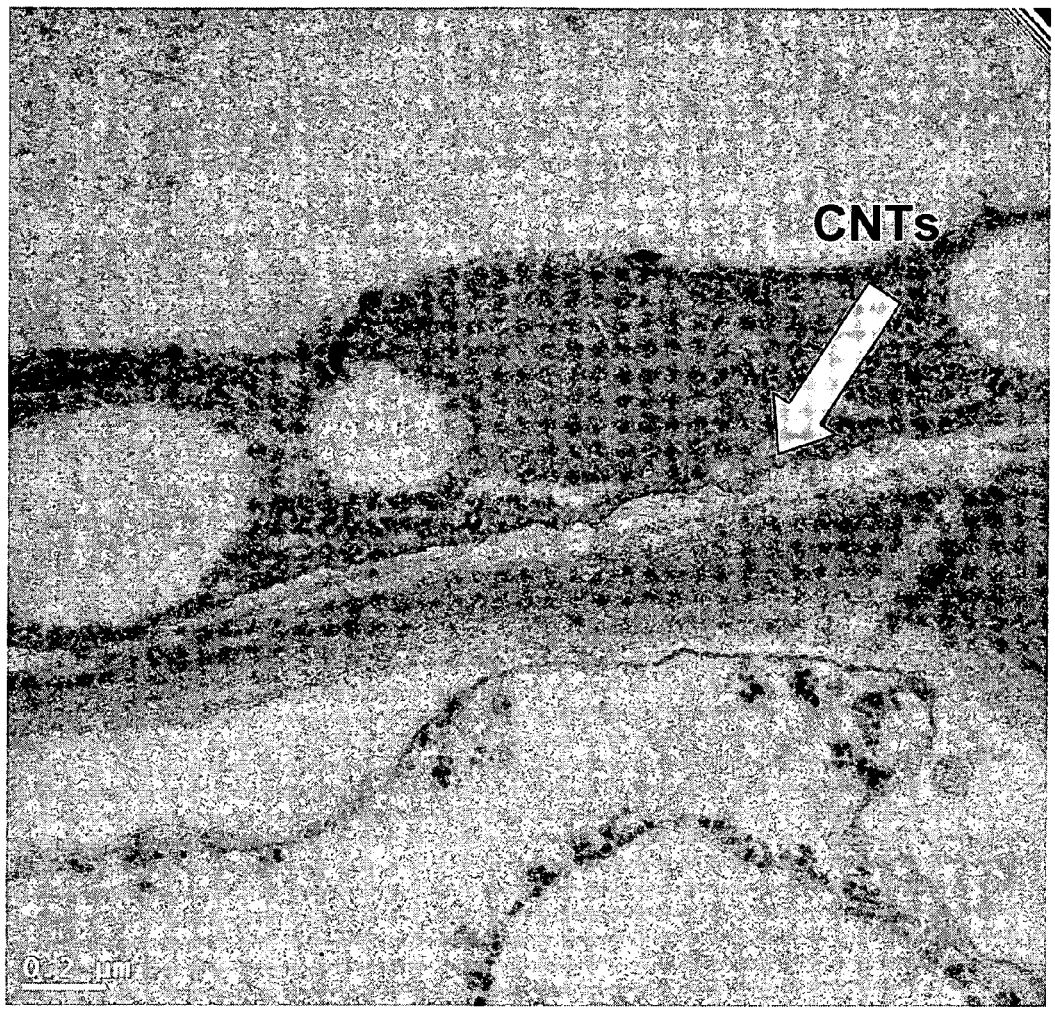
Figure 5-C

METHOD OF USING CARBON NANOTUBES TO AFFECT SEED GERMINATION AND PLANT GROWTH

TECHNICAL FIELD

The present invention relates to carbon nanotubes, and in particular, to the use of carbon nanotubes to affect seed germination and plant growth.

BACKGROUND ART

During the past decade there has been a rapid growth of research in the areas of nanomaterials and nanoscience because of the realization that these small size materials can be used in a multitude of industrial and biomedical processes. The great potential of using nanoscale particles for different biological and medical applications including gene and drug delivery, biosensing, diagnostic, tissue engineering was widely documented during last several years [Refs. 1-6].

Most investigations were focused on studying the effects of different nanomaterials on the cellular morphology, behavior and functions, and selective killing in order to understand how such structures would affect animals and humans at various levels [Refs. 7-11]. Moreover, thorough studies and reliable information regarding the effects of nanomaterials such as carbon nanotubes on plant physiology and plant development at the organism level are very limited. However, there is an extensive interest to investigate the ability of nanoparticles to penetrate plant cell walls and work as smart treatment-delivery systems in plants. Several research groups reported that different types of nanoparticles are able to penetrate plant cell walls. Thus, it was shown that gold-capped mesoporous silica nanoparticles (MSNs) were able penetrate cell wall and delivery DNA into plant cell by using a bombardment method [Ref. 12]. Lately, Liu and coauthors [Ref. 13] demonstrated the capability of single-walled carbon nanotubes (SWNTs) to penetrate the cell wall and cell membrane of tobacco cells. Additionally, methods of visualization of carbon-coated iron nanotubes in plant cells using pumpkin plants as model were reported [Ref. 14]. There is an extensive interest in applying nanoparticles to plants for agricultural and horticultural use [Ref. 15]. To achieve the goals of "nano-agriculture", detailed studies on the effects of nanotubes on seed germination and development of seedlings of valuable agricultural plant species are needed. Penetration of plant seeds could be more complicated as compared to plant cell walls and mammalian cell membranes due to the significant thickness of seed coat covering the whole seed [Ref. 16]. However, it was shown that seed coats of different plant species are selectively permeable to heavy metal ions such as $Pb^{2+}$ and $Ba^{2+}$ [Ref. 17]. Based on this observation it is logical to assume that some nano-size materials will be able to penetrate plant seed coats and affect seed germination. It would therefore be desirable to develop a method of increasing the probability and rate of seed germination using carbon nanomaterials. It would also be desirable to develop a method of increasing water uptake in seed using carbon nanomaterials. In addition, it would be desirable to develop a method for increasing vegetative biomass using carbon nanomaterials.

DISCLOSURE OF THE INVENTION

In the first preferred embodiment, the present invention is directed to a method for increasing the probability and rate of seed germination comprising placing one or more seeds on a nutrient medium, wherein said nutrient medium comprises an effective concentration of carbon nanomaterial.

In the second preferred embodiment, the present invention is directed to a method for increasing vegetative biomass comprising placing at least one seed on a nutrient medium, wherein said nutrient medium comprises an effective concentration of carbon nanomaterial.

In the third preferred embodiment, the present invention is directed to a method for increasing water uptake in seeds comprising placing at least one seed on a nutrient medium, wherein said nutrient medium comprises an effective concentration of carbon nanomaterial.

In the fourth preferred embodiment, the present invention is directed to a composition for coating seeds comprising a hydrophilic polymer and carbon nanomaterial.

In the fifth preferred embodiment, the present invention is directed to a method of coating seeds comprising applying a composition of matter comprising a hydrophilic polymer and carbon nanomaterial to the surface of a seed.

In the sixth preferred embodiment, the present invention is directed to a method of increasing the probability and rate of seed germination comprising applying a composition of matter comprising a hydrophilic polymer and carbon nanomaterial to the surface of a seed.

In the seventh preferred embodiment, the present invention is directed to a method of increasing vegetative biomass comprising applying a composition of matter comprising a hydrophilic polymer and carbon nanomaterial to the surface of a seed.

In the eighth preferred embodiment. the present invention is directed to a method of increasing vegetative biomass comprising applying a composition of matter comprising a hydrophilic polymer and carbon nanomaterial to the surface of a seed.

The exposure of carbon nanotubes to seeds of valuable crops, such as tomatoes can increase the germination percentage and support and enhance the growth of seedlings. Furthering these findings could result in significant developments of improved plants for the area of energy, by taking advantage of the enhancement in the biomass of the plants when they are exposed to nano-sized materials and fertilizers.

BRIEF DESCRIPTION OF THE DRAWINGS

These and other features, objects and advantages of the present invention will become better understood from a consideration of the following detailed description, appended claims and accompanying drawings where:

FIG. 1 includes low (A) and high resolution (B) TEM images of the CNTs obtained over Fe—Co/$CaCO_3$ catalyst, the weight loss profile and the oxidation rate of the CNTs (C) and their corresponding Raman scattering spectra (D).

FIG. 2 shows the effect of CNTs on tomato seed germination. (A) Time of germination and germination percentages of seeds incubated with and without CNTs during 20 days. Seedlings with developed cotyledons and root system were recognized as fully germinated in this experiment; (B) Phenotype of tomato seeds incubated during 3 days without (left) or with (right) CNTs on MS medium. Results are shown as average ±SE of three independent experiments.

FIG. 3 shows the effect of CNTs on growth and development of tomato seedlings. Results are shown as average ±SE of measurements of 10 plants per each condition. 27-day-old seedlings were used for all measurements. (A) Weight of total fresh biomass of tomato seedlings growing on medium with and without CNTs; (B) Length of stem of tomato seedlings growing on medium with and without CNTs; (C) Length of root system of tomato seedlings growing on medium with and without CNTs; (D) Phenotypes of 27-day-old tomato seedlings growing on medium with and without CNTs; (E) Phenotypes of 25-day-old tomato seedlings growing on medium without and with CNTs (10 and 40 μg/ml).

FIG. 4 shows mass loss (A) and moisture level (B) of seeds incubated with or without CNTs during 2 days.

FIG. 5 shows detection of CNTs inside tomato seeds incubated with CNTs by Raman spectroscopy (A); TEM images of the root system of 25-day-old tomato seedlings growing on medium without CNTs (B) and with CNTs (C).

BEST MODE FOR CARRYING OUT THE INVENTION

With reference to FIGS. 1-5, embodiments of the present invention may be described as follows.

Results and Discussion

Carbon Nanotubes Analysis. The multiwall carbon nanotubes (CNTs) used in this study were produced on a Fe—Co/$CaCO_3$ catalyst with a $Fe:Co:CaCO_3$ weight ratio of 2.5:2.5:95 using acetylene as carbon source at 720° C. The yield was found to be around 80%. The low and high-magnification TEM images of CNTs are shown in FIGS. 1A and 1B respectively. Thermogravimetric analysis (TGA) was performed to characterize the purity of the purified CNTs in an airflow rate of 150 ml/min. The first derivative of the TGA curve determines the decomposition temperature of the sample. FIG. 1C shows the weight loss profile of the purified nanotubes, which were heated from 25 to 850° C. at a rate of 5° C./min. The normalized TGA curve and its first derivative indicate a significant mass drop at around 551° C., which corresponds to the weight loss due to the combustion of the CNTs. The quantitative analysis revealed that after the single-step purification in HCl, the purity of the CNTs product was higher than 98%. Raman spectroscopy has been widely used to analyze the crystallinity and the diameter distribution of CNTs. The Raman scattering spectrum of the CNTs grown on Fe—Co/$CaCO_3$ is shown in FIG. 1D. The characteristic bands for CNTs are the D band, G band and the 2D band. The D band is present between 1305 and 1330 $cm^{-1}$ and is related to the presence of defects and impurities in the carbon nanotube. The G band, present between 1500 and 1605 $cm^{-1}$; is also known as the tangential band and arises from the $E_{2g}$ mode of the graphite plane. The G band position is relatively constant for CNT material excited at different energies [Refs. 18-20]. The last important mode observed in the Raman spectrum of CNTs is the 2D band or the second-order harmonic of the D band, which is often present between 2450 and 2650 $cm^{-1}$. The 2D band is also highly dispersive and associated with the degree of CNT crystallinity. The relative intensities between the G and the D band ($I_G/I_D$), and between the 2D and G band ($I_{2D}/I_G$) are found to be 0.81 and 0.63 respectively. These values indicate an inter-planar distance of 0.342 nm between the graphite layers, as shown by Yoshida et al [Ref. 21].

Carbon Nanotubes Affect the Germination Rate. To test whether the synthesized carbon nanotubes could affect germination and development of crop seedlings we placed sterile tomato seeds (cv. Micro-Tom) on standard agar Murashige and Skoog medium (MS medium) supplemented with different concentrations of CNTs (10, 20, 40 μg/mL). The MS medium without CNTs was used for control experiments. As shown in FIGS. 2A-B, addition of carbon nanotubes to agar medium was found to accelerate the process of seed germination and significantly shortened the germination time. Tomato seeds placed on medium with CNTs (10, 20, 40 μg/mL) germinated the $3^{rd}$ day while the tomato seeds placed on regular MS did not germinated at that time (FIG. 2B). The germination percentage rates during next days were dramatically higher for seeds that were treated with nanoparticles. The germination percentage for seeds that were placed on regular medium averaged 32% in 12 days and 71% in 20 days while germination percentage of the seeds placed on medium supplemented with CNTs averaged 74-82% in 12 days and 90% in 20 days (FIG. 2A). Seedlings with developed cotyledons and root system were recognized as fully germinated in this experiment.

We further investigated effects of CNTs on the growth and development of seedlings germinated on medium supplemented with nanoparticles (FIGS. 3A-E). Tomato seedlings germinated and developed on the medium with different concentrations of CNTs (10, 20, 40 μg/mL) exhibited a dramatic increase in vegetative biomass (FIG. 3A). Fresh weight of total biomass (leaves, stems and roots) increased 2.5 fold for the seedlings germinated and grown on CNTs containing mediums compared with seedlings developed on the standard medium. CNTs-exposed tomato seedlings had longer stems and were more developed but presented similar lengths of root system compared with control (CNTs non-treated) seedlings (FIG. 3B-E). The results (FIG. 3D) did not indicate any toxic effects of the CNTs on root development and root elongation of tomato seedlings, at least in the concentration ranges that were used. Water is a major required factor for plant seed germination. Mature seeds are relatively dry and need to uptake significant amounts of water before cellular metabolism and growth can resume. We hypothesize that the observed activation of germination by CNTs is based on role of CNTs in process of water uptake inside the seed embryo.

Carbon Nanotubes Promote Water Uptake Inside the Seeds. To better understand the mechanism of activation of plant seed germination by application of carbon nanotubes, we performed experiments to measure the level of moisture of the tomato seeds by thermogravimetric analysis (TGA). Total level of moisture (%) present in the tomato seeds was determined by measuring the total mass loss of the seeds (FIG. 4A-B) when heated from room temperature to 250° C. and maintained at this temperature for 120 minutes. First, we measured the level of moisture in dry tomato seeds before any treatments, and this data was used as reference. Then, dry seeds were placed on MS medium with and without CNTs and after 2-days of incubation, the moisture levels for the seeds (both exposed and not exposed to CNTs) were measured. It was founded that seeds that were exposed to CNTs had a significantly higher level of moisture compared with the seeds that were not treated with CNTs. Thus, 18.4% of moisture level was detected in dry seeds before the experiment; seeds exposed to CNTs accumulated about 57.6% of moisture and seeds unexposed to CNTs kept only 38.9% of moisture. This result suggested that carbon nanotubes could significantly enhance the water uptake inside tomato seeds.

One possible explanation of this observed effect could be based on the assumption that nanotubes are able to penetrate seed coat while supporting and allowing water uptake inside the seeds. To test such a possibility, Raman Spectroscopy was used to detect the possible presence of the CNTs inside the seed embryos exposed and un-exposed to CNTs. Raman Spectroscopy is a technique that can give accurate information for the presence of graphitic materials, such as CNTs, inside a biological systems, given the unique Raman spectrum of the CNTs and their strong scattering properties. For this experiment, tomato seeds were placed on regular agar MS medium (control) and MS medium supplemented with carbon nanotubes (40 μg/mL). Two days after the seeds were incubated under both conditions, they were removed from the medium, washed with water, opened by longitudinal cut, dried and the freshly exposed surfaces were analyzed by Raman Spectroscopy. Raman spectroscopy has the ability to monitor and identify the CNTs during their transportation from the medium to the seeds. The strong and specific Raman scattering properties of individual CNTs and their clusters, made it possible to use Raman Spectroscopy for monitoring the CNTs among the biological tissues of the seeds. As shown in FIG. 5, a Raman signal of the CNTs G band (1569 $cm^{-1}$) was detected inside seeds exposed to CNTs while no signal was detected in control seeds that were incubated on medium without nanoparticles. Even for relatively long acquisition times (over 80 seconds) the Raman spectra of the biological tissues did not show any peak at 1568 $cm^{-1}$ (which is therefore specific only to CNTs). Therefore this G band can be used as a marker for the presence of nanotubes and its intensity could reflect the amount of nanotubes present in the focal volume of the laser. The CNTs' corresponding G band was not observed when parts of the grown plants were further analyzed (roots, stems, leaves), which does not indicate that the CNTs were not present, but rather that possibly their amounts were below the detection level of the Raman spectrometer.

These results were further supported by high magnification TEM imaging of the roots collected from plants with and without exposure to CNTs (FIGS. 5B and C). It can be seen in FIG. 5C the clear morphology of several CNTs, which are completely missing in the images of the control samples. These studies indicate that the CNTs were able to penetrate both the seedlings as well as the root systems of the more developed plants.

These results clearly indicate that the various nanomaterials can be uptaken by the tomato seeds and significantly affect their biological activity, most probably by enhancing the amount of water that penetrates inside the seeds during the germination period.

The mechanism by which nanoparticles can support water uptake inside seeds is not clear yet. It is possible that nanoparticles can create new pores for water permeation by penetration of seed coat. Another explanation could be based on assumption that carbon nanotubes are able to regulate gating of existent water channels (aquaporins) in the coat of plant seeds.

An increased probability and rate of seed germination, increased vegetative biomass, and increased water uptake was also observed in seeds that were exposed to carbon nanomaterials in the concentration range of 0.1-200 μg/mL. Similar results are expected up to the toxic concentration limits of carbon nanomaterials.

Conclusions

Our results demonstrated, for the first time, that carbon nanotubes can penetrate thick seed coat and support to water uptake inside seeds. The activated process of water uptake, could be responsible for the significantly faster germination rates and higher biomass production for the plants that were exposed to carbon nanotubes. Molecular mechanisms of CNTs-induced water uptake inside plants seeds are not clear and require further investigation. However, observed positive effect of CNTs on the seed germination could have significant economic importance for agriculture, horticulture, and the energy sector such as production of biofuels.

Methods

Synthesis of carbon nanotubes. The multiwall carbon nanotubes (CNTs) used in this study were produced on a Fe—Co/$CaCO_3$ catalyst with a Fe:Co:$CaCO_3$ weight ratio of 2.5:2.5:95 using acetylene as carbon source at 720° C. First, the Fe:Co:$CaCO_3$ catalyst was prepared as follows: The distilled water solutions of the Fe($NO_3$)$_3$.9$H_2O$ and Co($CH_3$COO)$_2$.4$H_2O$ salts were poured over a CaCO3 suspension in water under continuous stirring. The pH of the solution was maintained constant at 7-7.5 by adding ammonia solution (25%). The solvent was evaporated on a steam bath under continuous stirring and the resulting solid matter was further dried overnight at 125° C. and powdered in a mortar.

For carbon nanotubes growth, 150 mg of the Fe:Co:$CaCO_3$ catalyst were uniformly dispersed onto a graphite susceptor and introduced into the quartz reactor (2 cm diameter and 80 cm length) positioned in the middle of a water-cooled copper coil connected to a high frequency generator (5 kW, 1.9 MHz). A nitrogen flow of 200 ml/min was introduced into the reactor for 15 minutes to remove the air, followed by inductive heating at 720° C. This process was followed by the administration of acetylene (3 ml/min) for 30 minutes. The removal of the catalyst from the CNT final product was done by ultrasonication in HCl (1:1) for 30 minutes, washing with distilled water, and drying overnight at 120° C. The efficiency of the reaction is defined as per cent ratio between the mass of product obtained after purification and the initial mass of catalyst. The morphology of the nanotubes was studied by scanning electron microscopy (SEM-JEOL 7100 FE), transmission electron microscopy (TEM- JEOL2100 FE). For this analysis, carbon nanotubes were dispersed in 2-propanol and sonicated for 10 min. A few drops of the suspension were deposited on the TEM grid, then dried and evacuated before analysis. Raman scattering studies of the CNTs were performed at room temperature using Horiba Jobin Yvon LabRam HR800 equipped with a charge-coupled detector, a spectrometer with a grating of 600 lines/mm and a He—Ne laser (633 nm) and Ar+ (514 nm) as excitation sources. The laser beam intensity measured at the sample was kept at 20 mW. The microscope focused the incident beam to a spot size of <0.01 $mm^2$ and the backscattered light was collected 180° from the direction of incidence. Raman shifts were calibrated with a silicon wafer at a peak of 521 $cm^{-1}$. Thermogravimetrical analysis (TGA Mettler Toledo 815e) was done in airflow (150 ml/min) and a heating rate of 5 deg /min.

Germination of tomato seeds. Seeds of tomato (cv. Micro-Tom) were sterilized by 10 minutes treatment with 50% Chlorox solution and then rinsed five times with sterile water. Sterile tomato seeds were placed on Murashige and Skoog medium (MS) without or with carbon nanoparticles (10, 20, 40 μg/mL) for germination. Sterile Magenta boxes were used for all germination experiments.

Transmission electron microscopy. Tomato samples (roots) were pinned onto Silgard-coated plastic petri dishes and overlaid with a fixing solution containing 2% paraformaldehyde, 2.5% glutaraldehyde, 1.5 mM calcium chloride ($CaCl_2$) and 1.5 mM ($MgCl_2$) In 0.05 M PIPES buffer, pH 6.9. Small pieces were then cut with a razor blade from the apical leaf tips and pinned in place to keep them submerged. Dishes were covered and fixation proceeded for 5.5 h at room temperature. Thereafter, leaf pieces were washed three times for 20 min each in 0.05 M PIPES buffer containing 1.5 mM $CaCl_2$ and 1.5 $MgCl_2$ and placed at 4° C. in the same solution overnight. Samples were washed one more time in the buffer rinse and then briefly postfixed at room temperature for 20 min in 1% osmium tetroxide, 0.8% potassium ferricyanide, 1.5 mM $CaCl_2$ and 1.5 mM $MgCl_2$ in 0.05 M PIPES buffer, pH 6.9, after which time Kodak Photo-flo was added (3.5% v/v) as a surfactant to reduce surface tension. After several minutes, pieces were unpinned from the Petri dishes and transferred to small shell vials containing fresh fixative without Photo-flo. Post-fixation continued for an additional 2.25 h. After fixing, tissues were restored to 4 C by rinsing in cold distilled water three times for 20 min each, and dehydrated in an ascending ethanol series from 10 to 70% ethanol (EtOH), in 10% increments for 20 min each. Tissues were then stained in 1% uranyl acetate in 70% EtOH for 1.5 h at 4° C., followed by two 5 min rinses in 70% EtOH, with the temperature brought back to room temperature during the second rinse. Dehydration was continued by washing tissues once in 85 and 95% EtOH and twice in 100% EtOH, 15-20 min per step. Finally, two washes in propylene oxide for 10 min each, preceded the embedment of material into Spurr's resin. Thin sections were cut from the embedded samples using an ultramicrotome equipped with a diamond knife. Sections were mounted on copper grids. The sections were examined by transmission electron microscope (JEOL 2100 FE).

Coating of seeds. The seeds may be coated with any biocompatible and biodegradable hydrophilic polymer including, but not limited to, a polyamine, polyurethanes, polyethylene glycol, or polyglycolic-lactic acid (PGLA). The hydrophilic polymer coatings can absorb and retain large volumes of water from the soil and this water retention is essential for seed germination. The polymer, however, need not be hydrophilic in nature. The polymer coatings range from 1 nm to 1 cm in thickness. The methods of coating are well-known to those skilled in the art and include brushing, air spray, electrospray, plasma deposition, ion deposition, electron deposition, and laser deposition.

The current invention also includes a method of coating seeds or plant tissues with carbon nanomaterials in both solid, liquid and gaseous (or aerosol) phases. These methods include, but are not limited to, electrospray, airbrush, atomic deposition, filtration, fluidized bed, continuous spraying on a conveying belt, and sol-gel technique. The biocompatible and biodegradable hydrophilic polymers are capable of forming composites with carbon nanomaterials including, but not limited to, single-walled nanotubes, multi-walled nanotubes, nanofibers, and fullerenes. The polymer, however, need not be hydrophilic in nature. The composite may be comprised of either one type or a combination of different types of carbon nanomaterials. The nanomaterials may also be chemically treated with functional groups, including, but not limited to carboxyl, carbonyl, and amine groups. The nanomaterials may also be attached to other polymers, biological molecules, organic or inorganic chemical structures, or other organic or inorganic nanomaterials. The carbon nanomaterials can be either mixed in the polymer matrix before deposition or deposited independent of the polymer system by layering (i.e. nanomaterial layer applied, then polymer layer applied, then nanomaterial layer applied, etc.). This polymer-carbon nanomaterial composite seed coating provides the carbon nanomaterial access to penetrate the seed coat. The nanomaterial can be taken up by the seed and bio-distributed into the plant tissues, thus altering gene expression and up-regulating the water channel genes.

The carbon nanomaterials are capable of binding proteins, genes, plasmids, growth factors, DNA, RNA, and antibiotics and deliver them into the plant tissue. The carbon nanomaterial then serves as a transport mechanism for these attached biological components into the seeds and the plants. Once inside the seed, these biological components can serve their well-known purposes of treating infection, facilitating growth, etc.

The seed may also be exposed to magnetic radiation, electric radiation, or electromagnetic radiation as means of increasing the temperature of the seed. The electromagnetic radiation includes, but is not limited to, laser radiation (from UV to Infrared), magnetic radiation, microwaves, radio frequency energy, and X-Ray. The increased seed temperature allows better uptake of nutrients and nanomaterials.

It was also found that plants that were watered with a solution comprising carbon nanomaterials displayed increased numbers of flowers and fruits. A solution of water and 50 µg/mL of carbon nanomaterials was prepared and applied to plants once per week. These plants exhibited up to twice as many flowers and fruits as those plants that were not watered with the solution of carbon nanomaterials. As an alternative to the liquid form, the carbon nanomaterials may be applied to the plants in a powder form, solid form, or aerosol form. The carbon nanomaterials may enter the plant through the plant's root, stem, or leaf systems. Similar results are expected with concentrations of carbon nanomaterials in the range of 0.1-200 µg/mL and up to the toxic concentration limits of carbon nanomaterials.

It was also found that plants that were exposed to a solution of carbon nanomaterials exhibited delayed leaf senescence and increased stability of chlorophyll. As an alternative to the liquid form, the carbon nanomaterials may be applied to the plants in a powder form, solid form, or aerosol form. The carbon nanomaterials may enter the plant through the plant's root, stem, or leaf systems. Similar results are expected with concentrations of carbon nanomaterials in the range of 0.1-200 µg/mL and up to the toxic concentration limits of carbon nanomaterials.

References

1. Oberdorster G, Oberdorster E, Oberdorster J. Nanotoxicology. An emerging discipline evolving from studies of ultrafine particles. Environ Health Perspect. 2005, 133 (7), 823-839.

2. Borm P J, Robbins D, Haubold S, Kuhlbusch T, Fissan H, Donaldson K, Schins R, Stone V, Kreyling W, Lademann J. The potential risk of nanomaterials: A review carried out for ECETOC. Part Fibre Toxicol. 2006, 3, 11.

3. Jayanth Panyam, and Vinod Labhasetwar. Biodegradable nanoparticles for drug and gene delivery to cells and tissue. Advanced Drug Delivery Reviews 2003, 55 (3), 329-347.

4. Benjamin S. Harrison, and Anthony Atala. Carbon nanotube applications for tissue engineering, Biomaterials, 2007, 28 (2), 344-353.

5. Laura P. Zanello, Bin Zhao, Hui Hu, and Robert C. Haddon. Bone Cell Proliferation on Carbon Nanotubes, Nanoletters 2006, 6 (3), 562-567.

6. Nadine Wong, Shi Kam, Michael O'Connell, Jeffrey A. Wisdom, and Hongjie Dai. Carbon nanotubes as multifunctional biological transporters and near-infrared agents for selective cancer cell destruction. PNAS 2005, 102 (33), 11600-11605.

7. Joe E K, Wei X, Anderson R R, and Lin CP. Selective cell targeting with light-absorbing microparticles and nanoparticles, Biophysical J. 2003, 84, 4023-4032.

8. Zharov V P, Galitovskaya E N, Jonson C, and Kelly T. Synergistic enhancement of selective nanophotothermolysis with gold nanoclusters: potential for cancer therapy. Laser Surg. Med. 2005, 37, 219-226.

9. Xian Xia, Michael Kovochich, Jonathan Brant, Matt Hotze, Joan Sempf, Terry Oberley, Constantinos Sioutas, Joanne I. Yeh, Mark R. Wiesner, and Andre E. Nel. Comparison of the Abilities of Ambient, and Manufactured Nanoparticles to Induce Cellular Toxicity According to an Oxidative Stress Paradigm. Nanoletters 2006, 6(8), 1794-1807.

10. Zhuang Liu, Corrine Davis, Weibo Cai, Lina He, Xiaoyuan Chen, and Hongjie Dai. Circulation and long-term fate of functionalized, biocompatible single-walled carbon nanotubes in mice probed by Raman spectroscopy. Proceedings of National Academy of Science, 2008, 105 (5), 1410-1415.

11. Geiser M, Rothen-Rutishauser B, Kapp N, Schurch S, KreylingW, Schulz H, SemmlerM, ImHof V, Heyder J and Gehr P. Ultrafine particles cross cellular membranes by non-phagocytic mechanisms in lungs and in cultured cells. Environ. Health Perspect. 2005, 113, 1555-1560.

12. Torney, F.; Trewyn, B.; Lin, V. S.-Y.; Wang, K. Mesoporous Silica Nanoparticles deliver DNA and chemicals into plants. Nature Nanotechnology. 2007, 2, 295-300.

13. Liu, Q.; Chen, B.; Wang, Q.; Shi, X.; Xiao, Z.; Lin, J.; Fang, X. Carbon nanotubes as molecular transporters for walled plant cells. Nano Lett. 2009, 9(3), 1007-10.

14. Gonzales-Melendi, P.; Fernandez-Pacheco, R.; Coronado, M. J.; Corredor E.; Testillano, P. S.; Risueno, M. C.; Marquina, C.; Ibarra, M. P.; Rubiales, D.; Perez-De-Luque, A. Nanoparticles as Smart Treatment-delivery Systems in Plants: Assessment of Different Techniques of Microscopy for their Visualization in Plant Tissues. Annals of Botany. 2008, 101, 187-195.

15. Joseph, T; Morrison, M. Nanotechnology in agriculture and food. 2006, www.nanoforum.org 16. Serrato-Valenti, G., Cornara L., Modenesi P., Piana M., Mariotti M. G. Structure and histochemistry of embryo envelope tissues in the mature dry seed and early germination of Phacelia tanacetifolia. Annals of Botany. 2000, 85, 625-634.

17. Wierzbicka, M., Obidzinska. The effect of lead on seed imbibition and germination in different plant species. J. Plant Sci. 1998, 137, 155-171.

18. Dresselhaus M. S., Dresselhaus G., Jorio A., Souza Filho A. G., Saito R., Raman spectroscopy on isolated single wall carbon nanotubes. Carbon 2002, 40, 2043.

19. Jorio A., M. A. Pimenta, A. G. Souza Filho, R. Saito, G. Dresselhaus, M. S. Dresselhaus, Characterizing carbon nanotube samples with resonance Raman scattering. New J. Phys. 2003, 5, 13.

20. M. S. Dresselhaus, G. Dresselhaus, R. Saito, A. Jorio, Raman spectroscopy of carbon nanotubes. Physics Reports, 2005, 409, 47-99.

21. Yoshida, A., Kaburagi, Y., Hishiyama, Y., Full width at half maximum intensity of the G band in the first order Raman spectrum of carbon material as a parameter for graphitization. Carbon, 2006, 44, 2330.

The present invention has been described with reference to certain preferred and alternative embodiments that are intended to be exemplary only and not limiting to the full scope of the present invention. Although the present invention is described with reference to carbon nanotubes and in particular multiwall carbon nanotubes, the invention is not so limited and may encompass other carbon nanoparticles and nanostructures, including nanotubes (both single walled and multiwalled), nanofibers, fullerenes and the like.

The invention claimed is:

1. A method for enhancing the germination and growth of seeds comprising the step of spraying a composition comprising a concentration of carbon nanomaterials to a surface of a plant seed, wherein said concentration of carbon nanomaterials is in the range of 0.1-200 µg/mL.

2. The method of claim 1 wherein said concentration of carbon nanomaterials is effective to increase the probability and rate of germination of said plant seed.

3. The method of claim 1 wherein said concentration of carbon nanomaterials is effective to increase vegetative biomass of a plant resulting from said plant seed.

4. The method of claim 1 wherein said concentration of carbon nanomaterials is effective to increase water uptake in said plant seed.

5. The method of claim 1 wherein said carbon nanomaterials are in a liquid phase.

6. The method of claim 1 wherein said carbon nanomaterials are in a gaseous phase.

7. The method of claim 1 wherein said carbon nanomaterials are in the form of an aerosol.

* * * * *